US012175551B2

(12) United States Patent
Ahrens et al.

(10) Patent No.: US 12,175,551 B2
(45) Date of Patent: Dec. 24, 2024

(54) SYSTEMS AND METHODS FOR INDUCING BEHAVIOR CHANGE

(71) Applicant: Patient Advocacy and Education, LLC, St. Louis, MO (US)

(72) Inventors: Thomas Steven Ahrens, St. Louis, MO (US); Thomas Matthew Ahrens, St. Louis, MO (US)

(73) Assignee: Viven Education, LLC, St. Louis, MO (US)

( * ) Notice: Subject to any disclaimer, the term of this patent is extended or adjusted under 35 U.S.C. 154(b) by 0 days.

(21) Appl. No.: 18/080,005

(22) Filed: Dec. 13, 2022

(65) Prior Publication Data

US 2023/0114477 A1 Apr. 13, 2023

Related U.S. Application Data

(63) Continuation of application No. 15/712,790, filed on Sep. 22, 2017, now Pat. No. 11,557,012.

(60) Provisional application No. 62/398,165, filed on Sep. 22, 2016.

(51) Int. Cl.
*G06Q 50/22* (2024.01)
*G16H 20/00* (2018.01)
*G16H 40/63* (2018.01)
*G16H 50/20* (2018.01)

(52) U.S. Cl.
CPC ............ *G06Q 50/22* (2013.01); *G16H 20/00* (2018.01); *G16H 40/63* (2018.01); *G16H 50/20* (2018.01)

(58) Field of Classification Search
CPC ........ G06Q 50/22; G16H 20/00; G16H 40/63; G16H 50/20

USPC .......................................... 705/2–3
See application file for complete search history.

(56) References Cited

U.S. PATENT DOCUMENTS

| 5,791,907 A * | 8/1998 | Ramshaw ............ G09B 23/285 434/323 |
| 9,101,261 B2 * | 8/2015 | Kim ...................... A61B 5/6887 |
| 10,452,896 B1 * | 10/2019 | Weise ..................... G06T 13/40 |
| 2004/0030987 A1 * | 2/2004 | Manelli .................. G16H 70/20 715/230 |
| 2004/0064298 A1 * | 4/2004 | Levine ................... G09B 23/28 703/11 |
| 2008/0081322 A1 * | 4/2008 | Fosbrook ............... G09B 19/00 434/262 |

(Continued)

FOREIGN PATENT DOCUMENTS

KR 20160000124 A 1/2016

OTHER PUBLICATIONS

International Search Report, International Patent Application No. PCT/US2017/052954, mailed Dec. 5, 2017 (11 Pages).

*Primary Examiner* — Michael Tomaszewski
(74) *Attorney, Agent, or Firm* — Lewis Rice LLC

(57) ABSTRACT

Generally, described herein are computer-implemented systems and methods for self-guided education in various aspects of health care. The described systems and methods effect behavior change through a functional relationship between the content of educational case packages comprising a plurality of displays, each of which has one or more completion conditions which must be completed by the user in accordance with a health care procedure to be practiced. The performance of the case by the user habituates behavior change through practice of a health care procedure.

10 Claims, 5 Drawing Sheets

(56) References Cited

U.S. PATENT DOCUMENTS

| | | | |
|---|---|---|---|
| 2008/0183069 A1* | 7/2008 | Fujimoto | G01T 1/1642 600/411 |
| 2010/0299156 A1* | 11/2010 | Jorgensen | G06Q 30/04 434/262 |
| 2012/0077167 A1* | 3/2012 | Weideman | G09B 7/04 434/262 |
| 2012/0130308 A1* | 5/2012 | Silkaitis | G16H 40/63 705/2 |
| 2014/0071072 A1* | 3/2014 | Itai | G06F 1/1626 345/173 |
| 2014/0085293 A1* | 3/2014 | Konoplev | A63F 13/55 345/419 |
| 2014/0100464 A1* | 4/2014 | Kaleal | A61B 5/486 600/595 |
| 2014/0141397 A1* | 5/2014 | Dunn | G09B 5/02 434/262 |
| 2014/0168216 A1* | 6/2014 | Kim | G06T 17/00 345/420 |
| 2014/0168217 A1* | 6/2014 | Kim | G06Q 30/0643 345/420 |
| 2014/0225978 A1* | 8/2014 | Saban | G06T 7/0012 348/14.07 |
| 2014/0244447 A1* | 8/2014 | Kim | G06Q 30/0643 705/27.2 |
| 2014/0285769 A1* | 9/2014 | Palanker | G16H 40/67 351/246 |
| 2014/0342333 A1* | 11/2014 | Knoche | G09B 5/02 434/262 |
| 2015/0046375 A1* | 2/2015 | Mandel | G06T 13/80 345/474 |
| 2016/0111021 A1* | 4/2016 | Knoche | G09B 7/00 434/262 |
| 2016/0125635 A1* | 5/2016 | Nam | A63F 13/58 715/764 |
| 2016/0163083 A1* | 6/2016 | Barmpoutis | G06T 17/20 345/419 |
| 2016/0180391 A1* | 6/2016 | Zabaneh | G06F 16/9535 705/14.58 |
| 2018/0018729 A1* | 1/2018 | Grimes | G06Q 30/0255 |
| 2023/0087969 A1* | 3/2023 | Fornwalt | G06N 20/00 705/2 |
| 2023/0353710 A1* | 11/2023 | Krol | G10L 25/51 |

* cited by examiner

SYSTEMS AND METHODS FOR INDUCING BEHAVIOR CHANGE

CROSS REFERENCE TO RELATED APPLICATIONS

This application is a continuation of U.S. Non-Provisional patent application Ser. No. 15/712,790 filed Sep. 22, 2017, which claims benefit of U.S. Provisional Patent Application No. 62/398,165 filed Sep. 22, 2016, the entirety of which is incorporated herein by reference.

BACKGROUND OF THE INVENTION

Field of the Invention

This disclosure pertains to the field of health care, and particularly to automated computer systems for inducing desired health care practices in a user.

Description of the Related Art

The old saw "practice makes perfect" has persisted for the simple reason that it is true. Study after study has shown that humans, like most animals, are creatures of habit, and generally learn best by doing. This basic concept is well known to any educator, as hours of lecture and explanation are no substitute for the pupil simply practicing the skill being taught.

This applies equally to health education. Poor health practices impose an enormous cost on society. Simple practices like hand sanitization can inhibit the spread of disease, sparing workers and employers downtime for illness, which imposes a massive cost on society. Although the Internet has made available high quality information concerning good health practices, users still must to know that such information exists, and seek it out and use it, in order to benefit from it. This alone prevents many people who would benefit from access to such information from ever encountering it. Moreover, even people who do see the information may not necessarily act on it.

Improving health care practices via behavior change is increasingly at the heart of health care. Whereas in generations past, health care was provided in a reactive model of diagnosing and treating acute disease, the focus is shifting to proactive healthcare based on preventing acute disease and efficiently managing chronic illness. With health care costs rapidly rising into the trillions of dollars in the United States alone, innovation is needed. According to one study, more than thirty percent of health care costs can be directly attributed to behaviorally influenced conditions, and almost seventy percent of total costs are heavily influenced by patient behaviors. Such behaviors range from pharmaceutical non-compliance to skipping therapies to not sanitizing one's hands after petting a dog.

It was long believed that people fail to adopt disease prevention strategies and submit to appropriate medical tests because they simply did not believe that disease posed a realistic threat, particularly when measured against the effectiveness of the preventive steps in question, and the cost (in terms of time, money, and hassle) in taking those steps. That is, a person's interest in avoiding illness is often too abstract, remote, or speculative to overcome a simultaneously present bias against changing behaviors, which is perceived by the patient as unlikely to be effective. However, this does not account for individual attitudes, beliefs, and other cognitive biases that influence behavior and also does not account for non-clinical preventive behaviors that influence health and disease.

Other behavioral models attempt to explain behaviors over which people have the ability to exert self-control, but do not. For example, despite the widespread availability of literature and messaging on the health complications of smoking, people continue to smoke. The planned behavior model, for example, focuses on intent, taking into account both motivation and ability to engage in, change, or discontinue behavior. Influencing factors include individual attitudes, subjective beliefs and norms, social norms, and perceived control. However, this model assumes the individual has the resources to understand which behaviors to adopt or change, as well as the opportunity and support to be successful in making such behavior changes. Also, other factors strongly influence choice in the moment, such as temporary emotional states, and the individual's degree of actual conscious control over behavior, which is often overestimated.

While these or other models have identified more than 400 barriers to general behavior change, there are five common reasons why people maintain poor health habits: (1) treatment is not perceived as valuable or necessary; (2) treatment is not convenient; (3) treatment cost is perceived as far exceeding its value; (4) ancillary effects of treatment are perceived as exceeding health benefits; and (5) the patient lacks sufficient knowledge to motivate behavioral change.

Each behavioral change theory has benefits and shortcomings, and no single theory completely explains behavior. However, a few key issues apply, regardless of the theory. First, if the patient does not have access to health care education, the patient will not receive information needed to set the groundwork for habituating good health care practices. Second, unstructured distribution of health care information can actually be counterproductive. For example, the Internet is both a blessing and curse, as the enormous volume of available information can be overwhelming and present patients with conflicting data and information. Additionally, information sources are generally obscure or unknown, or may be biased or misrepresent their qualifications or experiences. For example, users may instinctively distrust promotional literature about medications distributed by the pharmaceutical companies and analytical chemists who best understand a compound, yet blindly accept unfounded anecdotal stories posted by random, unknown strangers on the Internet, who relate only selective facts about their experiences and provide opinions without any apparent medical expertise.

Even if the user overcomes the noise-to-bandwidth ratio, information alone is not enough. Most models agree that presenting a person with information does not, by itself, result in habituation, although information is certainly a necessary component of education. Research shows that, when information is taught using psychologically effective teaching methods, habituation is more likely to result. Verbal presentations by an authority on the subject, for example, are far more impactful than reading the same information provided by the same person in writing. This is because people are fundamentally visual and social and more easily become engaged in a verbal presentation by an interesting authority figure. People become even further engaged in material that includes an "audience participation" element whereby the viewer becomes a part of the presentation, such as by interacting in some fashion with the presenter. Active engagement increases memory and retention and lays the groundwork for later recall and application, as the person's visual memory of the educational experience provides a more direct mental pathway to a similar scenario encountered later than does recollection of written materials.

Prior art attempts to habituate good health practices have fallen short for a number of reasons. First, teaching and practicing good health care habits using a live instructor is time-consuming and expensive. For one, a live instructor has a limited amount of time during the day to provide such instruction. Also, the patient must schedule time with the instructor in advance. The hassle of scheduling and making appointments alone discourages many patients from taking advantage of the opportunity to work with a live instructor. Additionally, many patients cannot easily travel to an instruction center in the first place. This may be due to limited physical mobility or lack of access to reliable transportation.

Additionally, providers are often overworked and running late, and patients often simply do not wish to schedule an appointment only to sit in a waiting room, sometimes for hours beyond the scheduled appointment time, waiting for their turn. Live instruction also typically imposes a cost or premium, which, in the modern era, is rarely covered entirely by health insurance. This imposes a concrete financial cost on the patient, particularly working adults, who may see no benefit to spending good money on receiving instruction on health care habits. Further, scheduling an appointment for instruction with a live instructor requires that the appointment be held at a time when the instructor is available. For working people in particular, it may be difficult to schedule a time during regular business hours to get away from work, but most live instructors are not likely to be available before or after business hours. Add in the lost time in traveling to the medical office, waiting one's turn, and traveling back, and the total time required to acquire basic instruction on medical care can constitute a substantial part of the day. For busy working professionals, this cost often vastly outweighs the perceived value of the instruction. For hourly workers, this time off may simply be unavailable.

Prior art attempts to deal with these shortcomings have also fallen short because they do not address all of these problems. For example, virtual medicine or "telemedicine" suffers many of the same problems in that these technologies still require a live instructor, still require that the instructor be available at the same time as the patient, and still require scheduling. This presents the same scheduling conflicts and time management conflicts as conventional live instruction. If "telemedicine" presentations are recorded for later viewing instead, the interactive aspect is lost, as the patient is essentially watching a video and has no opportunity to participate or engage meaningfully with the instructor.

In addition to the shortcomings of using an instructor, it is virtually impossible to monitor compliance. That is, doctors may simply provide literature or links to websites with information that the patient can view, or even interactive programs the patient can complete, but there is no effective way to monitor compliance with this program. When the patient returns to the doctor, and the doctor asks whether the patient has complied with the medical instructions, the patient can simply say yes and the doctor has no way of knowing whether the patient has complied or not. The doctor simply must take the patient at his word, as there is no practical way to verify the information provided by the patient. Also, although such materials have the advantage of not requiring a live instructor and thus having more flexibility to the patient for scheduling and convenience, these pre-printed materials are not customized in any way to the patient, and thus are likely to contain information that does not apply to a given patient. Such materials also lack the element of interactivity and engagement.

In addition to the shortcomings documented above, all of the prior art materials suffer the same problem of being non-habit forming. At a high level, the purpose of instruction and education is for the patient to habituate good health care practices. However, one-off instruction with a nurse or doctor is unlikely to result in long-term habituation of good health care habits or new routines. Further, a patient being handed an information pamphlet or directed to a website is also not likely to result in long-term habituation of good habits or new routines. This is because these prior art techniques lack various key elements to human behavior change, such as gratification, positive reinforcement, and, perhaps most importantly, repetition.

Current educational practices in the health care industry continue to lag behind. Medications are distributed with literature pamphlets that are simply thrown away, and patients often do not understand the relationship between a diagnosis and a therapy. What is needed in the art are systems and methods for providing health care instruction and education to patients which combine the customizability and reinforcement of a live instructor with the convenience and flexibility of paper materials.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein, among other things, is a method for practicing a health care procedure comprising: providing a server computer comprising: a non-transitory computer-readable storage medium having thereon a plurality of case packages, each of the case packages having an associated unique identifier and comprising a plurality of displays for practicing a health care procedure, the health care procedure including a plurality of steps to be performed in a predefined sequence, and each one of the displays corresponding to one of the plurality of steps, wherein each display in the plurality of displays includes at least one completion condition required to be completed for advancement through each display; providing a client device in communication with the server computer, the client device having a user input means and a screen, and a non-transitory computer-readable storage medium containing simulator software configured to execute any case package in the plurality of case packages; receiving at the server computer a request comprising a received identifier associated with one case package in the plurality of case packages; the server computer selecting from the plurality of case packages a selected case package having an associated unique identifier corresponding to the received identifier; receiving at the client computer the selected case package; the simulator software on the client device causing to be displayed on the screen a first display of the plurality of displays of the selected case package; via the input means, a user completing the completion condition of the first display by the user manipulating the first display in a manner mimicking the performance of the step of the health care procedure corresponding to the first display; only after the user completing the completion condition, displaying on the screen a next display in the plurality of displays.

In an embodiment of the method, at least one display comprises a visual element.

In a further embodiment of the method, the static image is selected from the group consisting of: a domestic setting; a hospital setting; a laboratory setting; and a clinical setting.

In a further embodiment of the method, the visual element is a static image of a domestic setting.

In a further embodiment of the method, the domestic setting is the user's domicile.

In a further embodiment of the method, at least one completion condition of the least one display comprises manipulating the visual element via the input means.

In a further embodiment of the method, the corresponding step of the health care procedure for the at least one display includes the use of a medical device; the visual element comprises an image of the medical device used in the corresponding step; the at least one completion condition comprises manipulating the visual image of the medical device in a manner mimicking the use of the medical device in the corresponding step.

In a further embodiment of the method, the image of a medical device is an image of the same type of medical device prescribed to the user.

In a further embodiment of the method, the image of a medical device is an image of the same model of the medical device prescribed to the user.

In a further embodiment of the method, the visual element is a body part.

In a further embodiment of the method, the client device comprises user profile data including the age, sex, and ethnicity of the user, and the visual element is a graphical representation of a body party customized to correspond to the age, sex, and ethnicity indicated in the profile data.

In a further embodiment of the method, the visual element is a photograph of the body part of the user.

In a further embodiment of the method, the corresponding step of the health care for the at least one display requires the use of a medical device on the body part; the visual element of a body part is a first visual element; the at least one display comprises a second visual element comprising an image of the medical device used on the body party in the corresponding step; the at least one completion condition of the at last one display comprises manipulating the image of the medical device with respect to the first visual element in a manner mimicking the use of the medical device on the body part in the corresponding step.

In a further embodiment of the method, the visual element is a photograph of a friend, relative, or neighbor of the user.

In a further embodiment of the method, the health care procedure is selected from the group consisting of: a diagnostic test; a preventative procedure; a physical therapy; an occupational therapy; and a pharmaceutical therapy.

In a further embodiment of the method, the client device communicates with the server computer via a telecommunications network.

In a further embodiment of the method, the method further comprises: for each display in the plurality of displays, via the input means, the user completing the at least one completion condition of the each display by the user manipulating each display in a manner mimicking the performance of the step of the health care procedure corresponding to each display; only after the user completing the at least one completion condition for all displays in the plurality of displays for the selected case package, receiving at the server computer an indication that the selected case package is complete.

DETAILED DESCRIPTION OF PREFERRED EMBODIMENT(S)

Figure 1:
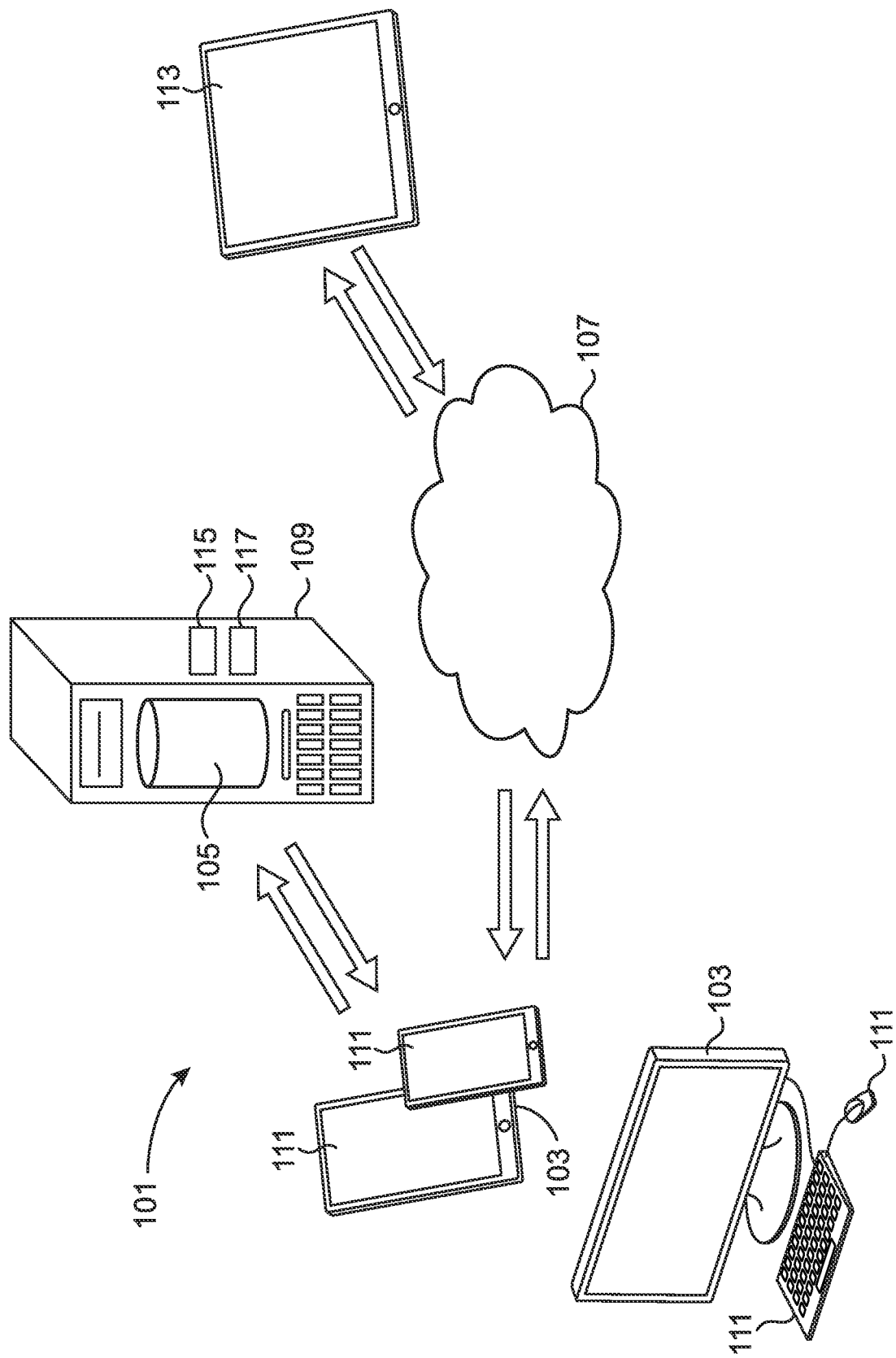
FIG. 1 provides a schematic diagram of a computer network system in an embodiment of the systems and methods.

The following detailed description and disclosure illustrates by way of example and not by way of limitation. This description will clearly enable one skilled in the art to make and use the disclosed systems and methods, and describes several embodiments, adaptations, variations, alternatives and uses of the disclosed systems and methods. As various changes could be made in the above constructions without departing from the scope of the disclosures, it is intended that all matter contained in the description or shown in the accompanying drawings shall be interpreted as illustrative and not in a limiting sense.

Generally, described herein are computer-implemented systems and methods for self-guided education in various aspects of health care. The described systems and methods effect behavior change through a functional relationship between the content of the educational cases, the user interaction required to compete the courses, and the sought-after behavior change.

Throughout this disclosure, the term "computer" describes hardware which generally implements functionality provided by digital computing technology, particularly computing functionality associated with microprocessors. The term "computer" is not intended to be limited to any specific type of computing device, but is intended to be inclusive of all computational devices including, but not limited to: processing devices, microprocessors, personal computers, desktop computers, laptop computers, workstations, terminals, servers, clients, portable computers, handheld computers, cell phones, mobile phones, smart phones, tablet computers, server farms, hardware appliances, minicomputers, mainframe computers, video game consoles, handheld video game products, and wearable computing devices including but not limited to eyewear, wristwear, pendants, fabrics, and clip-on devices.

As used herein, a "computer" is necessarily an abstraction of the functionality provided by a single computer device outfitted with the hardware and accessories typical of computers in a particular role. By way of example and not limitation, the term "computer" in reference to a laptop computer would be understood by one of ordinary skill in the art to include the functionality provided by pointer-based input devices, such as a mouse or track pad, whereas the term "computer" used in reference to an enterprise-class server would be understood by one of ordinary skill in the art to include the functionality provided by redundant systems, such as RAID drives and dual power supplies.

It is also well known to those of ordinary skill in the art that the functionality of a single computer may be distributed across a number of individual machines. This distribution may be functional (as where specific machines perform specific tasks) or balanced (as where each machine is capable of performing most or all functions of any other machine and is assigned tasks based on its available resources at a point in time). Thus, the term "computer" as used herein, can refer to a single, standalone, self-contained device or to a plurality of machines working together or independently, including without limitation: a network server farm, "cloud" computing system, software-as-a-service, or other distributed or collaborative computer networks.

Those of ordinary skill in the art also appreciate that some devices which are not conventionally thought of as "computers" nevertheless exhibit the characteristics of a "computer" in certain contexts. Where such a device is performing the functions of a "computer" as described herein, the term "computer" includes such devices to that extent. Devices of this type include but are not limited to: network hardware, print servers, file servers, NAS and SAN, load balancers, and any other hardware capable of interacting with the systems and methods described herein in the matter of a conventional "computer."

Throughout this disclosure, the term "software" refers to code objects, program logic, command structures, data structures and definitions, source code, executable and/or binary files, machine code, object code, compiled libraries, implementations, algorithms, libraries, or any instruction or set of instructions capable of being executed by a computer processor, or capable of being converted into a form capable of being executed by a computer processor, including without limitation virtual processors, or by the use of run-time environments, virtual machines, and/or interpreters. Those of ordinary skill in the art recognize that software can be wired or embedded into hardware, including without limitation onto a microchip, and still be considered "software" within the meaning of this disclosure. For purposes of this disclosure, software includes without limitation: instructions stored or storable in RAM, ROM, flash memory BIOS, CMOS, mother and daughter board circuitry, hardware controllers, USB controllers or hosts, peripheral devices and controllers, video cards, audio controllers, network cards, Bluetooth® and other wireless communication devices, virtual memory, storage devices and associated controllers, firmware, and device drivers. The systems and methods described here are contemplated to use computers and computer software typically stored in a computer- or machine-readable storage medium or memory.

Throughout this disclosure, terms used herein to describe or reference media holding software, including without limitation terms such as "media," "storage media," and "memory," may include or exclude transitory media such as signals and carrier waves.

Throughout this disclosure, the term "network" generally refers to a voice, data, or other telecommunications network over which computers communicate with each other. The term "server" generally refers to a computer providing a service over a network, and a "client" generally refers to a computer accessing or using a service provided by a server over a network. Those having ordinary skill in the art will appreciate that the terms "server" and "client" may refer to hardware, software, and/or a combination of hardware and software, depending on context. Those having ordinary skill in the art will further appreciate that the terms "server" and "client" may refer to endpoints of a network communication or network connection, including but not necessarily limited to a network socket connection. Those having ordinary skill in the art will further appreciate that a "server" may comprise a plurality of software and/or hardware servers delivering a service or set of services. Those having ordinary skill in the art will further appreciate that the term "host" may, in noun form, refer to an endpoint of a network communication or network (e.g., "a remote host"), or may, in verb form, refer to a server providing a service over a network (e.g., "hosts a website"), or an access point for a service over a network.

Throughout this disclosure, the term "cloud" and "cloud computing" and similar terms refers to the practice of using a network of remote servers hosted and accessed over the Internet to store, manage, and process data, rather than local servers or personal computers.

Throughout this disclosure, the terms "case" or "course" and "educational case" or "educational course," sometimes used in connection with the term "package" (as in, a "case package") refers to an educational software package implementing the delivery to a user of certain specific audiovisual content, the content being designed and presented to use habituate good health care practices in a user completing the case or course. The cases are generally multi-step serialized prompts requiring the user to interact with visual or audio-visual elements presented in the case in order to complete or solve the case. The cases may comprise still imagery, video, audio, and other interactive elements that can be manipulated by the user. The case is generally comprised of a plurality of displays shown to the user on a screen of a device, in a pre-defined sequence, and each display contains one or more completion conditions which must be completed in accordance with a health care procedure to be practiced. Completing all of the completion conditions on all screens in a case completes or "solves" the case.

A "completion condition" as used herein generally means any manner of using the input means of a computer device to manipulate the audiovisual or other interface components of a case display in a manner that mimics how the corresponding step of a health care procedure to be performed would be carried out in the real world. The term "mimic" and its derivatives, as used herein, means manipulation of the elements of a display in the simulation software, the manipulation requiring physical movement by the user that mirrors, copies, or replicates the physical movements or activities involved in performing the corresponding health care procedure in real life.

By way of non-limiting example, this may be as simple as using a mouse or touchscreen to drag an image of a closed first into contact with another fist, thereby causing a "fist bump" and practicing good hand hygiene. Also by way of non-limiting example, if the real-life procedure requires an insulin bottle to be inverted ten times, then the mimicking would involve manipulating the display to cause an image of an insulin bottle to be inverted ten times in the display. By way of clarification, this should be understood as distinct from clicking an interface button or otherwise interacting with the interface in a manner that indicates "completion" of the display but does not involve the use of the input means in a fashion that involves physically motion mirroring or mimicking the physical motions required in the corresponding real-life health care procedure.

The term "display," as used herein, generally refers to an interactive audiovisual presentation able to be shown to a user via a screen or other output means. A case package typically comprises a plurality of displays.

FIG. 1 depicts an embodiment of a system and method according to the present disclosure. The depicted embodiment comprises a user device (103) communicably coupled to a database (105) over a network. The database (105) is generally housed in a server computer (109). The user device (103) is also communicably coupled to a cloud computing platform (107). The server computer (109) may also be a physical, virtual, or logical computer in a cloud computing platform, which may be the same cloud computing platform (107). From an implementation standpoint, however, the server computer (109) is logically distinct from the cloud platform (107). Likewise, one of ordinary skill in the art will understand that "cloud computing" simply means remote hosting, and the cloud computing platform may be substituted with one or more local servers serving the same function in the system.

These systems implement a software distribution framework that is user- and/or group-specific, and which ultimately delivers a software package to the user device (103). The software package comprises instructions for running one or more short educational cases or courses on the user device (103). These cases are generally interactive, requiring the user to undertake specific, concrete interactions with the interface in order to complete the case. The interactions are themselves designed to habituate good health care practices in the user, and generally mirror the desired behavior changes.

Because behavior change is not unifactorial, each educational case generally embeds a plurality of drivers or techniques. These are generally aspects of the content and/or user interactions that may induce desired compliance in the user. Each individual user may respond to different combinations of drivers, and some may respond to none. Thus, the purpose of the system is not necessarily to cause any one particular user to change his/her behavior, but rather to influence a statistically significant subset of a larger group of users.

For example, a health insurer may offer policies at a reduced premium to all policyholders who complete a particular package of educational cases. Even if a relatively small percentage of those who complete the package ultimately adopt the desired behavior changes, this small amount of behavior change may still significantly reduce insured care, thereby offsetting the reduction in premiums. In other words, the change in behavior may be statistically significant compared to the overall scale and cost of health care services to justify a premium offset from an incentive standpoint. The benefits of these behavior changes include policyholders who are healthier and miss less time at their jobs and with their families, as well as a reduction in the quantity of health care services demanded, applying downward pressure on costs and resulting in fewer insured claims.

Generally, each case or course implements one or more drivers. In the preferred embodiment, each such driver is selected from the following six primary drivers: consistency; reciprocity; authority; consensus; scarcity; and positive regard. Other drivers may additionally or alternatively be implemented as well, but this disclosure focuses on these six drivers for sake of simplicity.

Consistency refers to the general human desire for consistency between word and deed. When humans say one thing but do another, they tend to experience a negative psychological response, often in the form of tension or anxiety. However, acting consistently with one's word tends to result in a positive psychological response. When a person says aloud that he or she will do something, that person is more likely to do it and may even change behavior to comply with his or her own verbal statement, even if the person has not promised or firmly committed to performing the stated action. This principle also works when one person says aloud an expected behavior from another person. For example, when Person A performs a favor for Person B and Person B thanks Person A, Person A may respond with, "You would have done the same for me." Because Person B has stated aloud a future behavior expectation from Person A, Person A generally experiences a psychological desire, to varying degrees depending on the individual, to conform future behavior in accord with this stated expectation.

Reciprocity refers to the principle of social psychology holding that individuals tend to "pay back" in kind what is received from others. Gift-giving is a common example. When Person A receives a gift from Person B on his or her birthday, Person A feels a social obligation to provide a gift to Person B on Person B's birthday. This sense of future obligation and social exchange is often the foundation of relationships, as those who consistently fail to exhibit reciprocity are perceived as free riders and often ostracized from groups. Continuing the above example, when Person A says, "You would have done the same for me," Person A is both setting up an expectation of future behavior with which Person B feels compelled to act consistently, and Person A is also reinforcing the principle of reciprocity, causing Person B to recognize a social debt owed and further inducing Person B to repay that debt. Because this is also consistent with the stated expectation of future behavior, Person B has two psychological drivers towards behavior change.

Authority refers to the human tendency to obey perceived authority figures, whether or not those figures have any obvious means of enforcing their instructions. So ingrained is the willingness to obey instructions that people can, in surprisingly large numbers, be induced to undertake behaviors that conflict with their personal conscience or moral code, the perhaps most famous example being the Milgram experiment. Common badges of authority figures include dress and carriage, as recognizable uniforms (e.g., lab coats for doctors) are a quick and effective visual cue to establish the identity and credibility of an authority figure, and a likable, confident carriage likewise induces a desire for compliance and obedience.

Consensus refers to the human desire to behave consistently with a peer group with which an individual identifies, and, conversely, to sometimes behave inconsistently with groups with which the individual does not identify. Related to the concepts of peer influence and peer pressure, consensus is a powerful influencer of behavior change, as any one individual can readily perceive the collective behavior of others but cannot definitively understand the thought process motivating those behaviors in each individual. The individual is thus generally induced to mimic the consensus behavior to avoid "sticking out" as unusual or non-compliant with a perceptible norm.

Scarcity refers to the human tendency to attribute inflated value to that which is rare or difficult to obtain over that which is abundant, and to desire to have access and control over same. Perhaps the simplest example of this driver is "Black Friday" shopping, which induces millions to camp out in retail shopping centers overnight to compete for coveted "deals." Capitalizing on this psychological phenomenon is a venerable sales tactic, as many buyers can be induced to make a decision to purchase immediately (i.e., change behavior) for fear of missing out on a good deal or missing out on the opportunity to possess the scarce item at all.

Finally, positive regard refers to general likability of the person suggesting a behavior change. Those who are positive, complimentary, happy, and cooperative can induce a desire for compliance among others.

One or more of these drivers is implemented via each case. Importantly, the driver is generally represented either through audiovisual components of the case, interface components, or both. The behavior change is sought to be induced by virtue of practicing a health care procedure with the assistance of computer software providing a simulation of the procedure to be performed. This may be best understood through reference to an example.

Figure 2A:
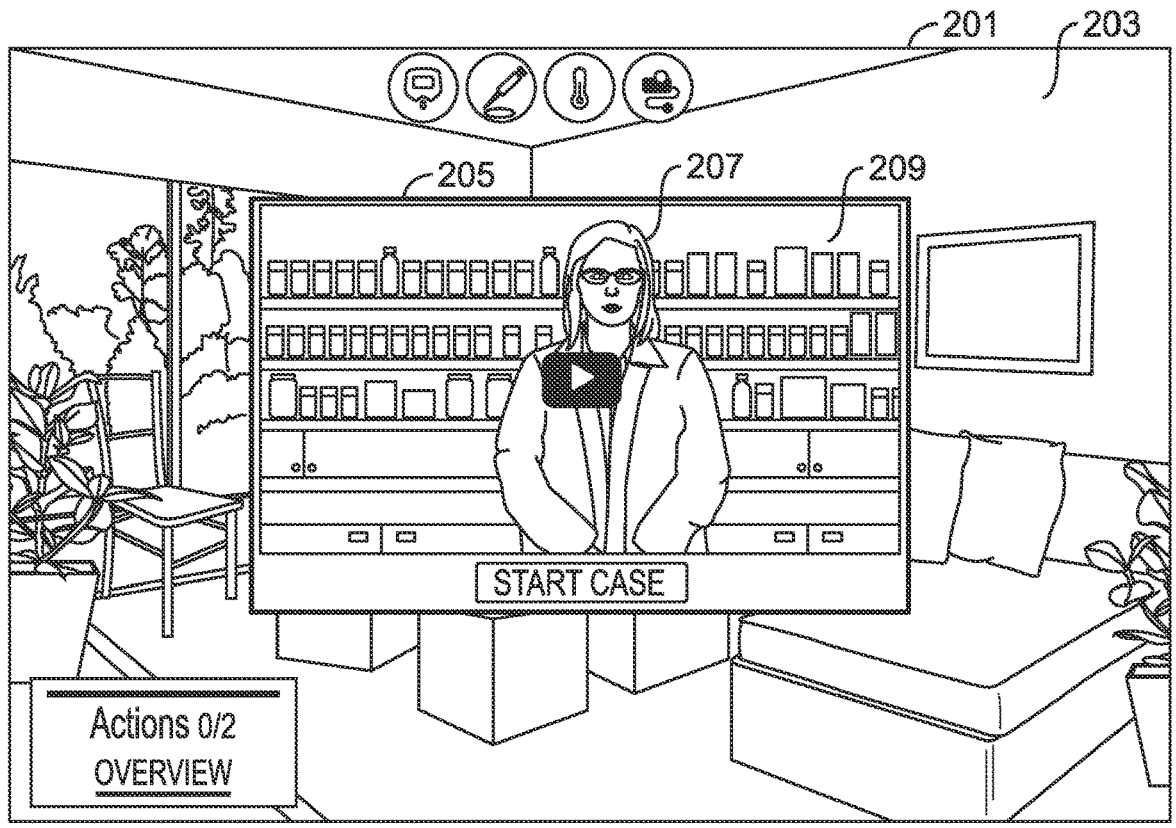
FIGS. 2A-2G provide screen shots from a computer end-user application implementing an embodiment of the systems and methods.

FIG. 2A depicts a case package (201) displayed on a user device (103). The depicted case package (201) concerns diabetic care and implements several behavior change drivers. A background image (203) is included in the case (201), depicting a cozy domestic setting. This is a subtle visual cue to the user that the behavior practiced in the case (201) is a behavior performed at home. In a preferred embodiment, the background image (203) is an image of the specific patient's own home, further reinforcing the location of the behavior, as human memory has been shown to have a strong location correlation component. Where the image is of the specific user's own home, the image may be captured by the user device (103) and uploaded, processed, stored, and packaged into the case for the specific user as described elsewhere herein. That is, although the same basic case is presented to multiple users, each user can receive a customized version with imagery specific to that user to reinforce the induced behavior change.

Also shown in FIG. 2A is a video playback component (205) depicting an authority FIG. (207) in a suitable environment (209). The depicted authority FIG. 207) is a pharmacist wearing a conventional pharmacist uniform. These elements implement a behavior change driver—authority—and reinforce it by depicting the authority FIG. 207) in a recognizable uniform, and providing information in an audiovisual format via an embedded video (205), while having the authority FIG. 207) depicted in a clinical or medical setting, further reinforcing the importance and character of the information conveyed. The specific content provided by the authority FIG. (207) is functionally tied to the behavior change desired, as well as to the content of the video, to the extent of at least the presence and appearance of the authority FIG. 207) and authority environment (209). Thus, the overall user experience in the case (201) presented in FIG. 2A is of an authority FIG. 207) in an authority setting (209) coming into the user's home via the background image (203) to provide medical information.

Figure 2B:
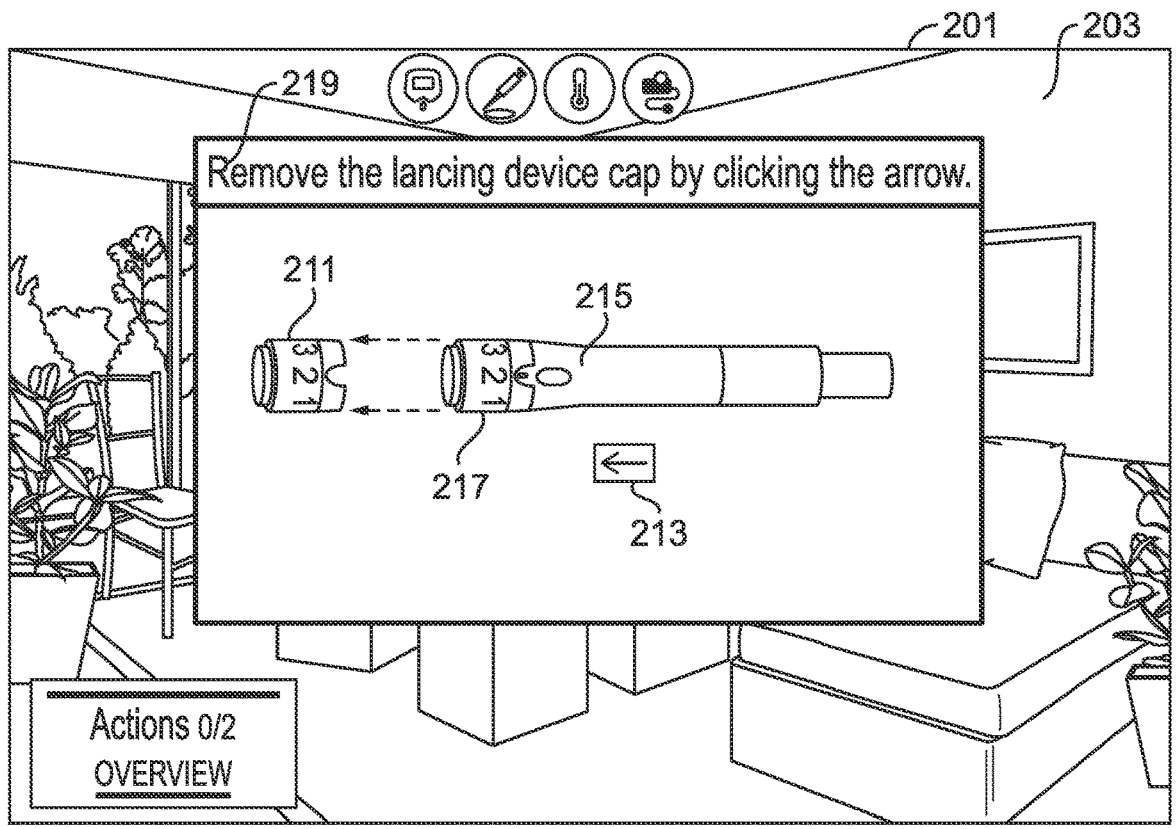

Referring now to FIG. 2B, different behavior change drivers are implemented. The background image (203) remains, but the authority figure video component (205) is now replaced by a static image of a medical device (215) pertaining to the procedure being taught—in this case, how to use a blood glucose lancing pen for diabetics. The depicted medical device (215) is a generic blood sugar lancing pen (215), but in a preferred embodiment, the user's own specific brand of lancing pen (215) is depicted. This may be done by associating an image of the user's specific pen (215) when the pen or prescribed or purchased, as described elsewhere herein. Depicting the user's specific device (215) further reinforces the induced behavior change.

In the depicted embodiment of FIG. 2B, the user is provided a brief written instruction (219) concerning how to proceed with the case (201). In the depicted embodiment, the instructions (219) tell the user to remove the lancing device cap (217) by clicking a user interface element (213), in this case, an arrow (213). The user does this by manipulating a user interface device (111), such as a mouse (111), keyboard (111), or touch screen (111) in the conventional fashion. Alternatively, the user may be asked to use the interface to select the cap (217) and slide it away from the pen (215) to remove it. In either case, in response to the user input, the image (215) changes to an animation to show the cap being removed (211). This part of the case (201) is thus solved and the user is presented with the next phase of the case (201).

Figure 2C:
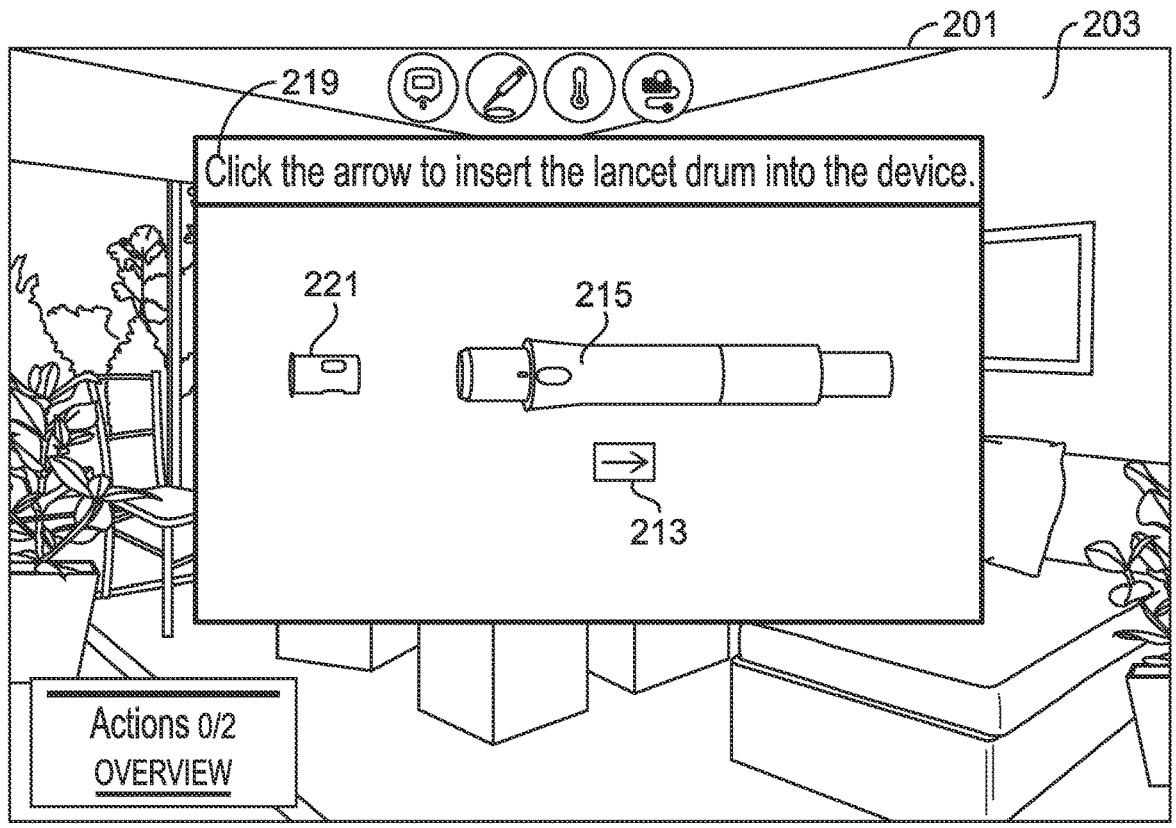
Figure 2D:
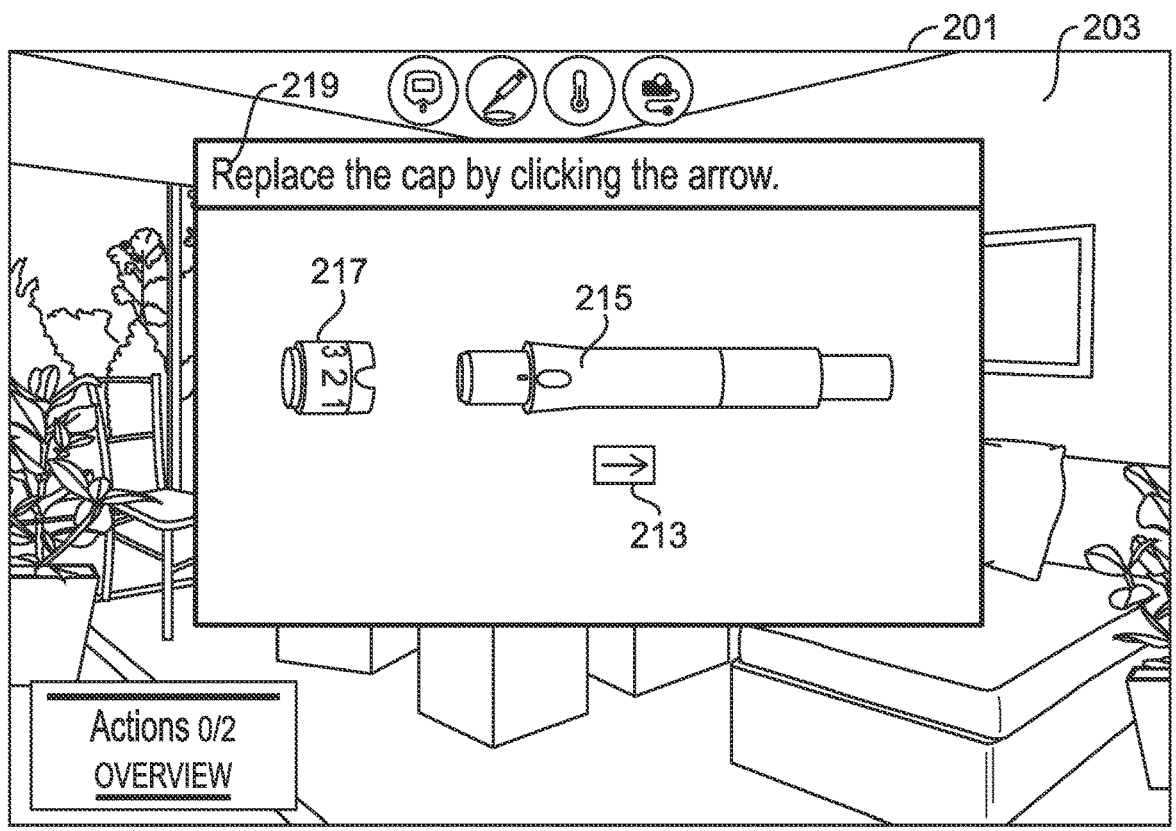

In FIG. 2C, the same basic interface is depicted, except that another component of the medical device (215) appears. In this embodiment, the component is a lancet drum, used to install a lancet in the pen. Again, the user manipulates the interface in a similar manner as in FIG. 2B, except in this case the user is installing a lancet in the pen (215) via a lancet drum (221). Again, it is preferred that the depicted drum (221) correspond to the equipment used by the specific user performing the case (201). In FIG. 2D, the same basic interface is depicted, except that the user is now asked to replace the lancet cap (217) on the pen (215). Again, the user manipulates the interface in a similar manner as in FIGS. 2B and 2C, this time replacing the cap (217) on the pen (215). The pen (215) is now ready to be used to draw blood.

Figure 2E:
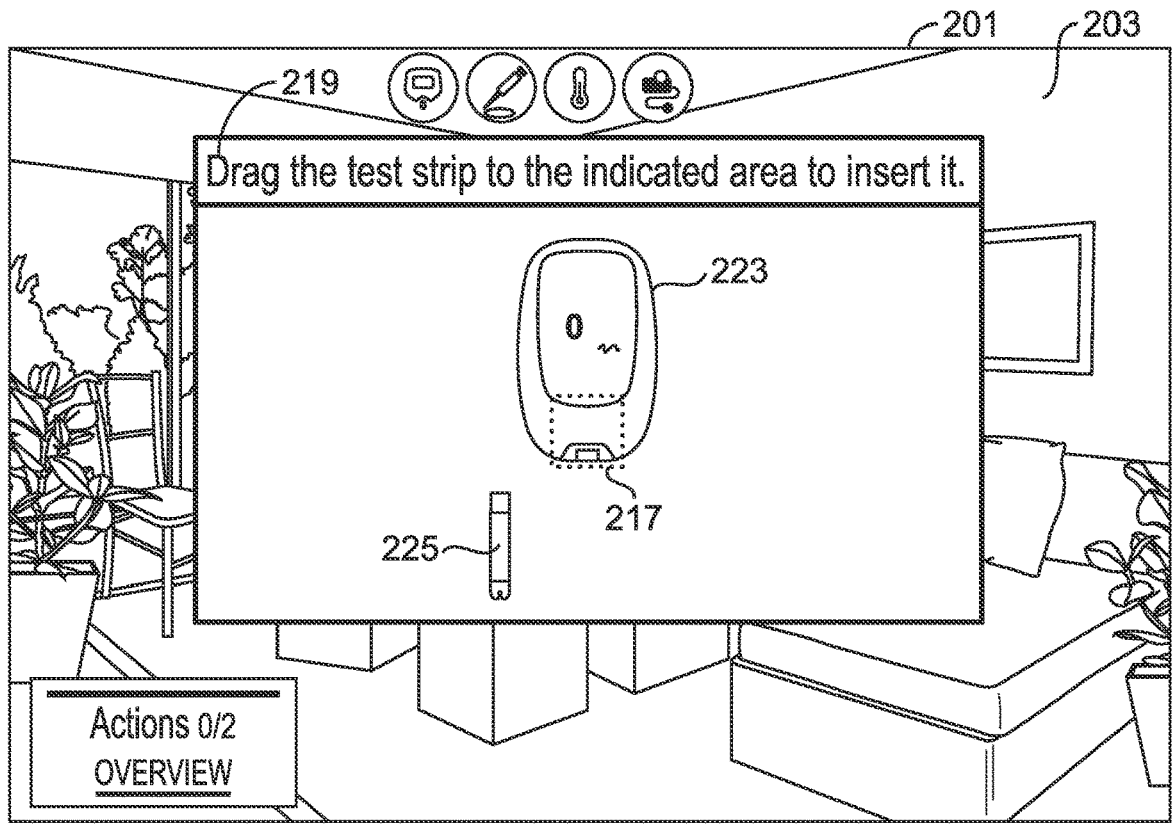

FIG. 2E depicts the next step, now showing a blood glucose testing device (223) and a blood glucose testing strip (225). Diabetics use one such strip each time they test blood sugar levels, and the strip (225) is inserted into a socket on the machine (223). Then a drop of blood is placed on an inlet of the strip (225), and the device then automatically draws the blood in and determines the blood sugar level, which is then reported on the device's display. In the depicted embodiment of FIG. 2E, the user is asked via the instructions (219) to drag the depicted test strip (225) to a specific location (227) on the blood sugar testing kit (223) to simulate placing a real strip in a real kit. As with the prior examples, it is preferred that the depicted device (223) and strip (225) be the same model and brand used by the specific user. In this part of the case (201), the user manipulates the interface to drag the strip (225) to the appropriate location, helping the user understand where on the device (223) the strip is to be inserted, and a visual cue is given via a highlighted or emphasized section (227) of the interface.

Figure 2F:
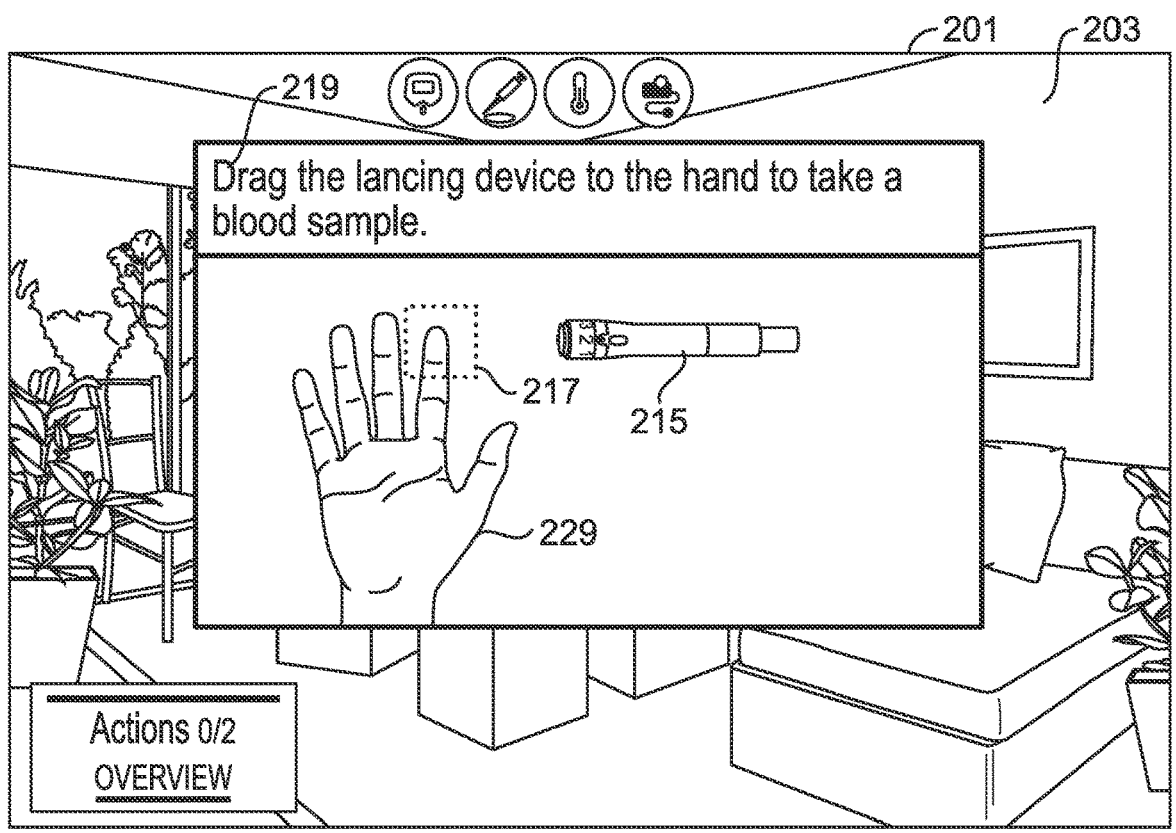

In the depicted embodiment of FIG. 2F, the user is instructed to lance the hand to draw blood. Diabetics are generally advised to lance the side of a finger. This is because repeated strikes can kill nerve endings, and the sides of fingers have both plentiful blood supply and reduced nerve density, lowering the chances of nerve damage and also reducing the discomfort to the patient. The pen (215), now prepared from prior steps, is depicted, along with a hand (229) and an emphasized or highlighted area (227) showing where to place the pen (215) to lance the finger. The user again manipulates the interface to drag the pen (215) to the appropriate position. Again, an image of the user's own hand (229) and pen (227) is preferred.

Figure 2G:
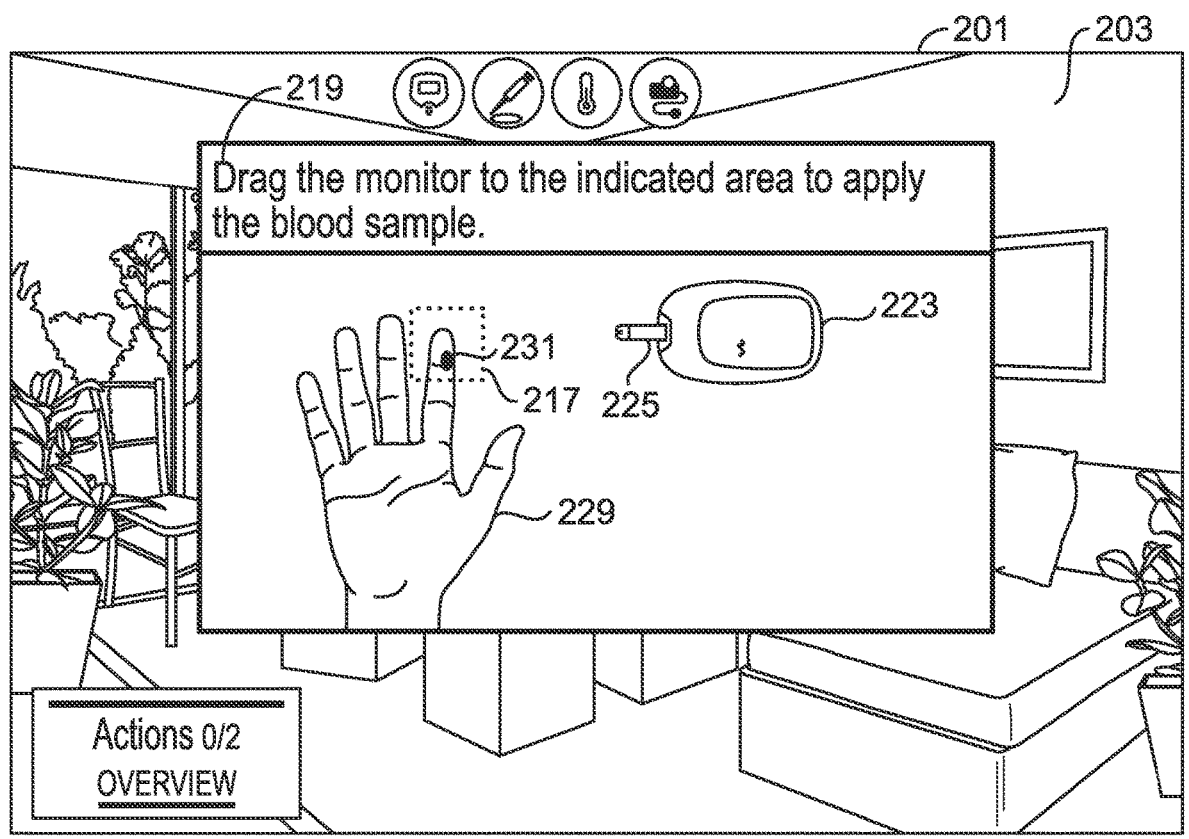

Finally, in the depicted embodiment of FIG. 2G, the case (201) concludes with the blood glucose test. The interface depicts the blood sugar testing device (223), now loaded with a testing strip (225), and the hand (229), now with a spot of blood (231) from the lancing pen (215) in the prior step. A highlighted or emphasized portion (227) provides a visual cue of where to move the testing device (223) to pick up the blood (231) and begin the test. The user again manipulates the interface to drag the testing kit (223) to the appropriate position (227), completing the case (201).

In an embodiment, the user is then prompted to take an action based on the blood glucose value (or, in embodiments using other cases, otherwise take an action based upon the results of the simulation). By way of example, if the blood glucose level is elevated, the user may be instructed to take a walk, or another simulation for an insulin injection may be shown. Alternatively, the user may not be provided any specific instruction, but rather given a multiple choice series of options and must select the most appropriate action that should be taken. The method thus develops critical thinking skills to habituate good health care practices.

Finally, at the conclusion of the case, the user may then be provided with a closing video or other congratulatory reward, which provides an immediate feedback mechanism confirming that the user has performed the steps correctly.

It should be noted that, although the user generally manipulates the computer in the conventional fashion by interacting with graphical elements of an interface using input means or devices (111), the purpose differs in that the software is not designed to allow the user to control and manipulate the computer, but rather the software is designed to control and manipulate the user. That is, the user is using the software for the sole purpose of practicing steps that the user is expected to take in the real, practical world. The software itself serves no particular application purpose with respect to the computer itself. The software is not mere "how-to" software providing multimedia instructions, but rather is an interactive educational package which requires the user to fully simulate the behaviors sought, in proper order, without shortcuts. This reinforces the entire behavior to the user and frames the user's perception of the steps involved and the amount of time they take.

Thus, when the user is later performing the steps in the real world and it has taken only a few minutes, the user can be confident that he or she has performed the steps correctly because the simulation took only a few minutes and included all of the same steps. It also reinforces to the user that uncomfortable or difficult actions are acceptable and correct. For example, many people are averse to drawing blood, but the simulation shows this as a normal part of the testing process, reinforcing to the user that doing so is a normal part of the health care routine. This may help some users overcome cognitive biases that might otherwise overwhelm their decision-making and cause them to abandon the process and discontinue attempting to monitor blood sugar levels, finding it too difficult, inconvenient, uncomfortable, or anxiety-inducing.

The cases (201) can also reinforce to users the normalcy in performing certain activities, particularly tedious or repetitive procedures. For example, Type I diabetics generally take two types of insulin injections, one long-term acting and one short-term acting, and these are usually mixed before injection. Proper mixing usually requires that the pen be inverted ten times. A simulation of how to load the pen with insulin would thus require the user to invert the digital version of the pen ten times, simulating the real-life scenario, even though the user has obviously understood how to manipulate the interface to invert the pen after one try. The requirement to invert ten times is not imposed because the user's interaction with the interface serves any computer application purpose; rather, the user goes through the exercise of inverting the digital pen ten times to induce and reinforce the desired behavior of inverting a real pen ten times before applying the injection.

As described above, the cases (201) are generally specific to a given behavior change that is desired. That is, a given case (201) may be for teaching a user how to use a diabetic lancing pen and blood glucose testing kit, but the case, when presented to a specific user, may include customizations for that specific user. Preferably, these customizations further induce the desired behavior. These are generally described above and generally comprise replacing generic components of the case (201) with user-specific components, such as background imagery of the user's own home or office, or of the user's physician's office, or another location appropriate for the case (201). Other customizations may include images of the user or the user's friends, family, or caregivers, and of the user's own medical equipment. These customizations may be added to system at virtually any point in the health care process, or by the user directly when using the end-user software as described elsewhere herein.

The content of the cases generally presents a scenario related to a medical condition of the user as well as a problem to be solved via a user action or interaction with the interface elements of the presented scenario. The scenario is not completed until the user performs all required actions and performs them in the correct manner, according to how the scenario is architected and programmed. This aspect is important because the scenario may be sponsored or required by a third party, which has an interest in the user completing the scenario correctly, such as a doctor, insurer, family member, caregiver, or even the user.

The completion aspect further appeals to other aspects of compliance, many of which are well-documented in gamification research, notably achievement and advancement. Again, the completion steps mirror real-world scenarios that the user will encounter in connection with a medical condition, thus reinforcing the desired behavior. This has the advantages of convenience and verifiability, as the user can complete the case at any time from his own home without having to schedule an appointment or meet with anyone, and because the system is computerized, the potential for falsely self-reporting completion is reduced.

It is also important to understand that the visual and interactive elements of the case displays are not arbitrary, but rather bear a functional relationship to the real-world health care procedure being taught. If the content of the cases were changed to vary from the procedure, the cases would be less effective and, if changed sufficiently, completely ineffective.

An example may further illustrate the typical structure of a set of cases. Continuing with the example of diabetic care, non-compliance with medications and/or regular blood glucose measuring are known to be significant contributing factors to poor blood sugar control, resulting in diabetic complications that impose costs on both the health care system and society at large. Thus, a physician, insurer, or other interested party may provide a reward or incentive for all those patients in a given group who complete a specific set of cases using the system and methods described herein. Typically, the user is presented with a plurality of cases concerning the same concept or behavior, as repetition is known to be a major factor in compliance.

Turning now to FIG. 1, the hardware systems used to implement this technology are depicted. The major depicted components are an end-user device (103), a server computer (109), a database system (105), a cloud computing service or platform (107), and a third party computer (113). Conceptually, the cases are delivered through a framework comprising case building software (115) and simulator software (117).

The end-user device (103) is typically a smart phone, tablet, or other computing device, having a user input means (111) operatively connected thereto. One of ordinary skill in the art will understand that an input means (111) is any user input device configured to provide input to the computer user. Examples of such devices include, but are not limited to: pointing devices (111) such as a mouse, trackpad, trackball, joystick, pointing stick, and the like; keyboard (111); tactile and/or touch-screen interface (111); audio input device, such as a microphone; motion-sensor, such as an accelerometer, gyroscope, or three-dimensional scanner; and composition devices using two or more of these or other technologies. The user device (103) generally also has a display means, such as a built-in display, attached monitor, projector, or other output mechanism known in the art. The end-user software includes simulator software generally installed on the end-user device (103), but this software may alternatively be accessible via a web site or other commonly distributed application delivery framework. The cases (201) are generally stored in a database (105) accessible by the user device (103) over a network. In the depicted embodiment, the cases (201) are built or constructed by a software program executing on a computer, generally the third party computer (113), but one of ordinary skill will understand that any computer in the system with appropriate hardware, including computer systems not depicted. The user device (103) may also be referred to as the client or client device herein.

When a new user first uses the system, the user creates, or is assigned, authentication credentials. These are preferably stored independently from the cases. In the depicted embodiment of FIG. 1, a cloud service (107) hosts user-specific data, such as authentication credentials, and manages the authentication process. That is, when a user loads the simulator software on the user device (103), the simulator connects over a network to an authentication system in the cloud (107). If the user is authenticated, the authentication system may return one or more tokens, cookies, or other identifiers indicating a set of one or more cases (201) in the database (105) for the user. These specific cases (201) may be associated with the user for any number of reasons.

In an embodiment, the system may have, or have access to, demographic data about the user, and cases may be selected for the user based upon such demographic data. Factors such as age, sex, ethnicity, religion, and country of origin may influence which cases (201) are presented, as certain diseases and conditions are more common among members of specific demographic groups.

In an embodiment, a case is associated with a user in connection with the provision of health care services. For example, a diabetic patient visiting an endocrinologist may be prescribed a new blood glucose meter and testing strips. At the point of diagnoses and prescription, the system may be updated by the physician or his/her staff via a physician client computing device (not depicted), which again may be anything from a smart phone or tablet to a desktop computer. Cases for diabetes may thus be associated with the user, and those cases may be automatically customized for the user, based upon the specific glucose meter prescribed.

Cases may be prescribed based upon a set of cases selected by the doctor, or by somebody else, such as the insurer. Cases may also be specific to the medication or devices or therapies prescribed, and thus may also be selected, at least in part, based upon the recommendations of a device manufacturer, therapist, or pharmaceutical manufacturer. Cases may also be selected based upon specific aspects of the patient, or may be recommended based upon the patient's medical history, or by a friend, family member, or other caregiver.

An aspect of the systems and methods described herein is effectively infinite customized ability. This customized ability comes primarily, but not exclusively, in the form of customizing the appearance of the various aspects of the cases to match, as closely as possible, the day-to-day life and environment of the patient. By way of example, and not limitation, as described elsewhere herein, where a case depicts a background photograph, such as a domestic setting, a photograph of the patient's own home may be substituted for stock photography. Similarly, still photography of an authority figure, such as a pharmacist or physician, may be replaced by a photograph of the patient's own primary care physician, or another doctor or caregiver. Also by way of example and not limitation, photographs of the medical devices or medicines taken by the patient may be substituted for the specific devices or medicines taken by the specific patient.

Further customizations are also specifically contemplated. Such further customizations may include aspects such as altering the skin tone of elements of the simulation intended to represent the patient to match the patient's own coloration. Similarly, the apparent age of a depicted element intended to represent the patient may also be altered to match that of the patient. Thus, where the simulation would depict, for example, a finger being pricked to draw blood, the appearance of the hand may be altered to match the age and pigmentation of the user. This could be done based on a provided photograph of the user, or based upon demographic information provided to the system, which could be used as a proxy. For example, if the patient is indicated as being a Caucasian in her 70's, the depicted hand may be pigmented generally as a Caucasian, with age lines, and perhaps fingernail polish or longer fingernails, indicating a female hand. By contrast, where the patient is a young black male, the pigmentation may be darker, and the hand may appear younger, and lack adornment.

Further customizations may be possible, such as including messages from friends or family members to reinforce the habituation of the desired health care practices. For example, an image of a parent may appear for younger users, or of a child for older users, providing customized messages from the family member, and may possibly include an image of the family member, further reinforcing the desired habit. The simulation thus has the advantages of a live instructor in that the experience is customized to the specific user, but has the convenience of standalone lessons such as paper pamphlets, which the user can consume in the convenience of his or her own home at any time, without having to schedule an appointment or travel to a medical office. Because the simulations are repeatable, habituation is more likely, and compliance can be confirmed and monitored through the use of computer software. Techniques for doing so are well known in the art, as the completion of a lesson can simply be communicated to a server system and stored in memory for later access by a party desiring to monitor or confirm the compliance with the lessons.

Referencing again to the depicted embodiment of FIG. 1, individual users are generally managed on the server side through a unique identifier for the user associated with a set of profile data. A user may also be associated with one or more groups, also generally identified via a unique identifier associated with a set of profile data for the group. Such groups may be organized along any categorical lines, such as but not necessarily limited to demographical groups and/or commercial groups (e.g., sets of users insured by the same carrier). This allows the system to assign appropriate courses to a user based on group membership. By way of example and not limitation, an insurance carrier may offer a premium discount to all policyholders who complete a given set of courses. All qualifying users may then be associated into a group and, by virtue of that group membership, assigned the courses selected by the insurance carrier.

Also, in an embodiment, certain courses may be assigned only to individuals with certain demographic characteristics. For example, courses related to pregnancy may be assigned only to users in a "pregnancy" group. Also by way of example and not limitation, certain courses may concern subject matter only relevant to one sex or the other, such as courses related to certain aspects of reproductive health. Also be way of example and not limitation, certain courses may concern subject matter primarily relevant to certain ethnicities, as some diseases disproportionately afflict members of certain ethnic groups.

Referring now to FIG. 1, cases and case data are typically stored in a memory of the computer server (109) and are provided to the user client computer (103) via a network connection. The server (109) may comprise a builder (115), which is used to construct new cases. The cases are typically stored in a database (105), which is communicatively and operatively connected to the server (109). Once a user has logged in (typically via the cloud (107)), a user identifier associated with the user is retrieved from cloud (107) storage and provided to the server (109) via the client computer (103). The received user IDs at the server (109) is used to retrieve a set of applicable cases from the database (105), which are then returned to the user device (103) by the server (109). The available cases may then be displayed to the user, typically via a display (111) on the user device (103). The user may then manipulate the user interface of the user device (103) to select the case to be completed. The user may then select the case, which is then loaded and displayed on the user device (103) from the database (105), and the user may complete the case as described elsewhere herein. Once the case is completed, an indication of same is sent to the server (109) from the user device (103), which is then recorded in a memory for later retrieval to confirm completion and compliance.

Customization may take place at any point in this process. In the simplest example, when a case is first downloaded to the user device (103), the case will contain generic imagery. For example, if the case depicts a domestic setting, stock photography of an attractive middle class household may be depicted. Similarly, if the case depicts an authority figure, such as a doctor or pharmacist, a generic representation of a doctor or pharmacist may be shown. The user may customize the case at that point. This may be done by, for example, using a camera or other imaging device associated with the user device (103) to capture a photograph of the user's own home. This domestic photography may then be integrated into the case to replace the stock photography. Additionally, the custom domestic photograph captured by the user may be uploaded to the server (109) and stored in connection with the user's identifier. This photograph may then be used in all subsequent or other cases performed by the user which utilize domestic photography. For example, if the user later requests another case that includes domestic photography as a driver, the user's own prior custom domestic photograph will be downloaded instead of the stock photography. Alternatively, this customization may be stored in association with user profile data via the cloud (107). Other photographs or customizations may also be inputted by the user, such as a photograph of the user, or of the user's hand or another body part, which photograph may be used to further customize a simulation as described elsewhere herein. By way of example and not limitation, these customizations may cause elements of the simulation which represent the user to be customized to match the user's age, ethnicity, appearance, or other similar aspects.

Customization may also take place at the point of prescription or case. For example, when a doctor prescribes a medicine or device, the doctor can associate the prescribed device with the patient at the doctor's office. Thus, when the doctor prescribes the device, and the case is to be completed, the cases are automatically customized with the specific device prescribed by the doctor. This may also comprise selecting specific cases for the specific device, as medical devices serving similar purposes may nevertheless have subtly different nuances in how they operate. This has the advantage of the simulation automatically being updated when the patient downloads it, without the patient having to take any further steps. Again, this customization data may be stored in the server or in the cloud (107) in connection with the user's identifier.

Customization may also take place at the point of procurement, such as when the user acquires a pharmaceutical product from a pharmacy. Different pharmaceutical manufacturers will have different appearances, shapes, and sizes for the same medication. This can be confusing to patients who expect their medication to always appear the same way. Particularly for patients who take multiple medications, these differences in medication appearances can reduce compliance or increase the risk of overdose or misuse. Thus, since the pharmacy is aware at the point of procurement which specific manufacturer's medication was given to the user, the pharmacy can access the system and associate that specific medication with the user profile. Thus, when the user later participates in a simulation case pertaining to that medication, the medication will appear in the case having the same appearance as the actual medication the user acquired at the pharmacy. This would allow two different patients receiving the same medication, but manufactured by two different production lines, to each have the visual appearance of the medication in their cases match the actual medication each patient received. Because the particular mediation can even vary from pharmacy to pharmacy, or from refill to refill at the same pharmacy, the pharmacist can access the system to update the medication for the patient with each refill, ensuring that the visual appearance of the medication in the cases remains accurate.

In embodiments involving such customizations, the customization data is preferably stored in the cloud in association with user specific information. That is, the user's demographic information and customizations are typically stored in the cloud (107), are retrieved in connection with user authentication, may be stored locally on the user device (103), and then may be integrated into a downloaded case. Alternatively, such information may be provided to the server (109) and integrated into the case at the server (109), with the completed, customized case being downloaded back to the user device (103). However, it is generally preferred that the customization take place at the user device (103), reducing the number of times that user-customized information is transmitted. This is particularly important to the extent that the user customizations may include photographs of individuals, as the user generally would prefer that such materials not be transmitted any more than is necessary. Customizations by a doctor, pharmacist, or other third party may generally be done via a third party computer system (113), as shown in FIG. 1.

To make and use the described systems and methods, one of ordinary skill would use existing computer hardware and software systems and develop additional required programming to implement the simulation software and facilitate the other operations. The computer operations required to implement the systems and methods are known to one of ordinary skill in the art and can be carried out using any modern programming language or development platform. The specific programming techniques and the hardware and software architectures will vary from embodiment to embodiment, depending upon, among other things, the programming language(s) and development platform(s) used, as well as the hardware systems and end-user environment in which the systems will be used. These selections are primarily a matter of taste, preference, and resources. Any suitable platform (e.g., Windows™, MacOS™, Linux™) is contemplated, as well as any reasonably modern programming language (e.g., Java, C++, C#).

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method comprising:
a client device receiving from a server computer a case package comprising a plurality of displays for automated, computer-aided training for a medical health care procedure, each of said displays comprising a placeholder image of a domestic setting, and at least one of said displays comprising a visual representation of a body part, said visual representation having a placeholder represented age and a placeholder represented skin pigmentation;
receiving at said client device image data of a user of said client device;
receiving at said client device image data of a domicile of said user;
said client device:
modifying said case package by replacing said placeholder image of a domestic setting in each of said plurality of displays with said received image data of said domicile;
modifying said placeholder representation of said age of said body part to correspond to the age of said user based on said received image data of said user;
modifying said placeholder representation of said skin pigmentation of said body part to correspond to the skin pigmentation of said user based on said received image data of said user;
displaying on a screen of said client device a first display of said plurality of displays of said modified case package, said first display being a display in said at least one of said displays comprising a visual representation of a body part, said displayed first display including said image data of said domicile, and said displayed representation of said age of said body part corresponding to said age of said user based on said image data of said user, and said displayed representation of said skin pigmentation of said body part corresponding to said skin pigmentation of said user based on said image data of said user.

2. The method of claim 1, wherein said medical health care procedure is selected from the group consisting of: a diagnostic test; a preventative procedure; a physical therapy; an occupational therapy; and a pharmaceutical therapy.

3. The method of claim 1, wherein said client device communicates with said server computer via a telecommunications network.

4. The method of claim 1, wherein said medical health care procedure includes a plurality of steps to be performed in a predefined sequence, and each one of said displays corresponding to one of said plurality of steps, wherein each display in said plurality of displays includes at least one completion condition required to be completed for advancement through said each display.

5. The method of claim 4, wherein said client device comprises a user input means and a non-transitory computer-readable storage medium containing simulator software configured to execute any case package in said plurality of case packages.

6. The method of claim 5, further comprising:
via said input means, said user completing said completion condition of said first display by said user manipulating said first display in a manner mimicking the performance of said step of said medical health care procedure corresponding to said first display;
only after said user completing said completion condition, displaying on said screen a next display in said plurality of displays;
after said user successfully completes all displays in said plurality of displays, said client device transmitting to said server computer an indication that said user has successfully completed all displays in said plurality of displays;
receiving and storing, at said server computer, said transmitted indication of completion; and
confirming compliance of said user with said for automated, computer-aided training by retrieving said stored indication of completion.

7. The method of claim 6, wherein at least one completion condition of said least one display comprises manipulating said visual element via said input means.

8. The method of claim 7, wherein:
said corresponding step of said medical health care procedure for said at least one display includes the use of a medical device;
said visual element comprises an image of said medical device used in said corresponding step;
said at least one completion condition comprises manipulating said visual image of said medical device in a manner mimicking the use of said medical device in said corresponding step.

9. The method of claim 8, wherein said image of a medical device is an image of the same type of medical device prescribed to the user.

10. The method of claim 9, wherein said image of a medical device is an image of the same model of said medical device prescribed to the user.

* * * * *

UNITED STATES PATENT AND TRADEMARK OFFICE
CERTIFICATE OF CORRECTION

| | |
|---|---|
| PATENT NO. | : 12,175,551 B2 |
| APPLICATION NO. | : 18/080005 |
| DATED | : December 24, 2024 |
| INVENTOR(S) | : Thomas Steven Ahrens and Thomas Matthew Ahrens |

It is certified that error appears in the above-identified patent and that said Letters Patent is hereby corrected as shown below:

In the Claims

Claim 7, at Column 20, Line 39, should read:
"condition of said at least one display comprises manipulating"

Signed and Sealed this
Fourth Day of February, 2025

Coke Morgan Stewart
*Acting Director of the United States Patent and Trademark Office*